US010488393B2

(12) United States Patent
Kavusi et al.

(10) Patent No.: US 10,488,393 B2
(45) Date of Patent: Nov. 26, 2019

(54) DEVICE AND METHOD FOR SELF-REFERENCED CONFIDENCE TEST

(75) Inventors: Sam Kavusi, Menlo Park, CA (US); Christoph Lang, Cupertino, CA (US)

(73) Assignee: Robert Bosch GmbH, Stuttgart (DE)

( * ) Notice: Subject to any disclaimer, the term of this patent is extended or adjusted under 35 U.S.C. 154(b) by 2143 days.

(21) Appl. No.: 12/895,361

(22) Filed: Sep. 30, 2010

(65) Prior Publication Data

US 2012/0079897 A1 Apr. 5, 2012

(51) Int. Cl.
G01N 33/48 (2006.01)
G01N 33/487 (2006.01)
G06G 7/58 (2006.01)

(52) U.S. Cl.
CPC .......................... *G01N 33/48707* (2013.01)

(58) Field of Classification Search
CPC .................................. G06F 19/20; G06F 19/22
See application file for complete search history.

(56) References Cited

U.S. PATENT DOCUMENTS

| 8,673,650 | B2* | 3/2014 | Pi ................................. 436/164 |
| 2004/0185445 | A1 | 9/2004 | Fang |
| 2005/0186554 | A1 | 8/2005 | Temov et al. |
| 2010/0144052 | A1 | 6/2010 | Pi |
| 2011/0195853 | A1 | 8/2011 | Kavusi et al. |

FOREIGN PATENT DOCUMENTS

| WO | 9945148 A1 | 9/1999 |
| WO | 02090964 A1 | 11/2002 |
| WO | 2011050463 A1 | 5/2011 |

OTHER PUBLICATIONS

Angenendt, "Progress in protein and antibody microarray technology," Drug Discovery Today, Apr. 2005, pp. 503-511, vol. 10, No. 7, Elsevier, Heidelberg, Germany (9 pages).
Asanov et al., "Regenerable Biosensor Platform: A Total Internal Reflection Flourescence Cell with Electrochemical Control," Analytical Chemistry, Mar. 15, 1998, pp. 1156-1163, vol. 70, No. 6, American Chemical Society, USA (8 pages).
Domnanich et al., "Protein microarray for the analysis of human melanoma biomarkers," Sensors and Actuators B: Chemical, May 20, 2009, pp. 2-8, vol. 139, Issue 1, Elsevier, Seibersdorf, Austria (7 pages).
Drabovich et al., "Smart Aptamers Facilitate Multi-Probe Affinity Analysis of Proteins with Ultra-Wide Dynamic Range of Measured Concentrations," Journal of the American Chemical Society, May 16, 2007, pp. 7260-7261 and S1-S5, vol. 129, Issue 23, ACS Publications, Canada (7 pages).
Gooding et al., "Electrochemical modulation of antigen-antibody binding," Biosensors and Bioelectronics, Sep. 15, 2004, pp. 260-268, vol. 20, Issue 2, Elsevier, Australia (9 pages).
Heaton et al., "Electrostatic surface plasmon resonance: Direct electric field-induced hybridization and denaturation in monolayer nucleic acid films and label-free discrimination of base mismatches," Proceedings of the National Academy of Sciences, Mar. 27, 2001, pp. 3701-3704, vol. 98, No. 7, National Academy of Sciences, Washington, D.C. (4 pages).
Hood et al., "Systems Biology and New Technologies Enable Predictive and Preventative Medicine," Science Magazine, Oct. 22, 2004, pp. 640-643, vol. 36, U.S.A. (4 pages).
Jackola et al., "Entropy-favored human antibody binding reactions with a non-infectious antigen," Molecular Immunology, 2008, pp. 1494-1500, vol. 45, Elsevier Ltd, U.S. (7 pages).
Jones et al., "A quantitative protein interaction network for the ErbB receptors using protein microarrays," Nature, Jan. 12, 2006, pp. 168-174, vol. 439, Nature Publishing Group, Cambridge, U.S. (7 pages).
Kingsmore, "Multiplexed protein measurement: technologies and applications of protein and antibody arrays," National Review Drug Discovery, Apr. 2006, pp. 310-320, vol. 5, No. 4, U.S. (23 pages).
Liron et al., "Voltage-induced inhibition of antigen-antibody binding at conducting optical waveguides," Biosensors & Bioelectronics, 2002, pp. 489-494, vol. 17, Washington, D.C., (6 pages).
O'Grad et al., "Dynamic Control of Protein-Protein Interactions," Langmuir, 2008, pp. 316-322, vol. 24, No. 1, American Chemical Society, Washington, D.C., (8 pages).
Ohmura et al., "Combinational Use of Antibody Affinities in an Immunoassay for Extension of Dynamic Range and Detection of Multiple Analytes," Analytical Chemistry, Jan. 2003, pp. 104-110, vol. 75, No. 1, American Chemical Society, U.S. (7 pages).
Roy et al., "Effect of pressure on antigen-antibody complexes: modulation by temperature and ionic strength," Molecular Immunology, 1999, pp. 1149-1158, vol. 36, Elsevier Science Ltd., U.S. (10 pages).
Selby, "Interference in immunoassay," Ann Clin Biochem, 1999, pp. 704-721, vol. 36, United Kingdom (18 pages).

(Continued)

*Primary Examiner* — Eric S Dejong
(74) *Attorney, Agent, or Firm* — Maginot Moore & Beck LLP

(57) ABSTRACT

A system and method of providing a confidence test in one embodiment includes determining a first quality metric based upon a first and a second test environment wherein the second test environment is different from the first test environment, exposing a sample to a plurality of test sites, establishing the first test environment at a first of the plurality of test sites, establishing the second test environment at a second test site, obtaining a first detection signal associated with the first of the plurality of test sites exposed to the sample and at the first test environment, obtaining a second detection signal associated with the second of the plurality of test sites exposed to the sample and at the second test environment, determining a second quality metric based upon the first detection signal and the second detection signal, and comparing the second quality metric with the first quality metric.

19 Claims, 9 Drawing Sheets

(56) References Cited

OTHER PUBLICATIONS

Service, "Proteomics Ponders Prime Time," Science Magazine, Sep. 26, 2008 pp. 1758-1761, vol. 321, AAAS, The Netherlands (4 pages).

Tan et al., "Evaluation of gene expression measurements from commercial microarray platforms," Nucleic Acids Research, 2003, pp. 5676-5684, vol. 31, No. 19, USA (9 pages).

Wong et al., "Dynamic control of biomolecular activity using electrical interfaces," Soft Matter, 2007, pp. 267-274, vol. 3, The Royal Society of Chemistry, UK (8 pages).

Yarmush et al., "Immunoadsorption: Strategies for Antigen Elution and Production of Reusable Absorbents," Biotechnol. Prog., 1992, pp. 168-178, vol. 8, American Chemical Society and American Institute of Chemical Engineers, Piscataway, USA (11 pages).

Edman et al., Electric field directed nucleic acid hybridization on microchips, Nucleic Acids Research, Dec. 24, 1997, pp. 4907-4914, vol. 25, No. 24, Oxford University Press, Great Britain. (8 pages).

O'Connor et al., "The dependence of radioimmunoassay detection limits on antibody affinity", Journal of Immunological Methods, Oct. 27, 1997, pp. 181-189, Elsevier Science Publishers, The Netherlands. (9 pages).

Saaem et al., "Preliminary studies on the rapid detection of *Staphylococcus aureus* using a microfluidic device and nanopatterned hydrogels", Bioengineering Conference, 2007, Mar. 1, 2007, pp. 234-235, Bioengineering Conference, 2007, USA. (2 pages).

Sosnowski et al., "Rapid Determination of Single Base Mismatch Mutations in DNA Hybrids by Direct Electric Field Control", Proceedings of the National Academy of Sciences of USA, Feb. 1, 1997, pp. 1119-1123, National Academy of Science, USA. (5 pages).

International Search Report and Written Opinion in corresponding PCT application (i.e., PCT/US2011/061909), completed Feb. 8, 2012 (14 pages).

European Search Report and Written Opinion corresponding to European Application No. 11793619.5, dated Mar. 16, 2016 (10 pages).

\* cited by examiner

DEVICE AND METHOD FOR SELF-REFERENCED CONFIDENCE TEST

FIELD

This invention relates to diagnostic tests and more specifically to affinity based diagnostic tests.

BACKGROUND

Diagnostic tests that can be performed at the point of care of an individual, such as at the bedside of a patient, at a care provider location, or at the home of the patient, are becoming increasingly popular. The promise of such diagnostic tests is described, for example, by Leroy Hood et al., "Systems Biology and New Technologies Enable Predictive and Preventative Medicine," *Science* 306, no. 5696 (Oct. 22, 2004): 640-643. Depending upon the particular diagnostic test, the substance tested may be human body fluids such as blood, serum, saliva, biological cells, urine, or other biomolecules. Diagnostic tests are not, however, limited to biomolecules since testing may be further desired on consumables such as milk, baby food, or water.

As described by Stephen F. Kingsmore, "Multiplexed Protein Measurement: Technologies and Applications of Protein and Antibody Arrays," *Nature Reviews, Drug Discovery* 5, no. 4 (April 2006), pages 310-320, and Robert F. Service, "PROTEOMICS: Proteomics Ponders Prime Time," *Science* 321, no. 5897 (Sep. 26, 2008): 1758-1761, multiplexed measurement platforms such as protein arrays are a promising diagnostic technology that are currently being explored in conducting the diagnostic tests described above. Such multiplexed measurement platforms frequently incorporate affinity based sensors which are considered to be the state-of-the-art in detection of biomarkers.

Affinity based sensors function according to a "key-lock" principal in which a molecule with very high association factor to the marker of interest is used for detection. For example, a pregnancy test kit may incorporate a monoclonal antibody specific to a β-subunit of hCG (βhCG). The antibody is conjugated with a tag, e.g., gold, latex, or fluorophore, which is used for detection. If the targeted molecule binds with the conjugated antibody, the tagged key-lock pair will be detectable such as by a visible test line.

ELISA plates and microarrays (e.g., Nucleic Acid, peptide, and protein) incorporate a similar principal. FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample 18 is then added to the well in which the primary antibody 12 is immobilized. Next, the sample is incubated for some time. During incubation, the blocker 16 prevents the molecules of interest in the sample from binding to the surface of the substrate 14 in order to avoid false binding. During incubation, some of the molecules of interest 18 become bound with some of the antibodies 12 as depicted in FIG. 2. After incubation, the remaining sample is washed to remove the unbound primary antibodies 18.

Subsequently, a secondary antibody 20 with a bound label 22 is added to the well, incubated, and washed resulting in the configuration of FIG. 3. As depicted in FIG. 3, the labeled secondary antibodies 20 are bound to the molecules of interest 18 that are in turn bound to the antibodies 12. Accordingly, the number of labels 22 bound by the antibodies 20 to the antigen 18 is proportional to the concentration of the target antigen. Depending on the label used, the number of labels can be finally detected using colorimetry, amperometry, magnetometry, voltammetry, luminescence, or fluorescence detection. Other label-free antibody processes such as surface plasmon resonance may alternatively be used.

Various issues arise when incorporating an affinity based multiplexed biomolecule detection platform in conducting tests including bias and variation. These issues are detailed by Philipp Angenendt, "Progress in Protein and Antibody Microarray Technology," *Drug Discovery Today* 10, no. 7 (Apr. 1, 2005), pages 503-511, and Paul K. Tan, et al., "Evaluation of Gene Expression Measurements from Commercial Microarray Platforms," *Nucleic Acids Research* 31, no. 19 (Oct. 1, 2003), pages 5676-5684. In summary, molecules immobilized on a substrate can denature and lose their binding capacity. The extent of such degradation varies depending upon the immobilized molecule and the type and conditions of immobilization. Consequently, some areas of a particular microarray may always express or not express regardless of whether or not a molecule of interest is present in a sample.

Various approaches to mitigate the errors encountered when using multiplexed measurement platforms have been developed including the provision of a coefficient of variation indicative of the consistency between various test sites on a platform or the consistency between various platforms. A coefficient of variation, however, provides only an indication of the consistency between test sites or platforms. A coefficient of variation does not account for inconsistencies between samples such as the presence of interfering molecules. Moreover, performing control experiments to identify interfering molecules or other variations in the sample or processing of a multiplexed measurement platform are prohibitive in many applications.

Another issue that arises in the development of diagnostic testing devices is the complexity of associations in gene/biomarker discovery. These complex associations may lead to unexpected variations in biological assays as reported by David a Lacher, et al., "Estimate of Biological Variation of Laboratory Analytes Based in the Third national Health and Nutrition Examination Survey," *Clinical Chemistry*, 51, no. 2 (Feb. 1, 2005), pages 450-452, And Alan Aderem, "Systems Biology: Its Practice and Challenges," *Cell* 121, no. 4 (May 20, 2005), pages 511-513.

The complexity of the associations in gene/biomarker discovery makes development of readily understandable depictions of the associations, such as creation of pathways, heat maps, interaction networks, etc., problematic. Moreover, the manner in which a molecule associates varies according to different test environments. One color coded approach to depicting an interaction network is described by Richard B. Jones, et al., "A Quantitative Protein Interaction Network for the ErbB Receptors Using Protein Microarrays, *Nature* 439, no. 7073 (Jan. 12, 2006), pages 168-174. Development of the color coded depiction, however, was the result of extensive effort and is thus generally prohibitive.

Accordingly, a need exists for a device and method of providing a confidence test for an assay. A further need exists for providing a quality metric for assays such as multiplexed assays, e.g., protein arrays, competitive assays, or bead based arrays, as well as low cost devices, e.g., lateral flow devices, or other biochips. A device and method which provides a quality metric without the need of a control sample unique to the array would be beneficial. A device and method which provides a quantitative evaluation of gene/biomarker associations under different test conditions would be further beneficial.

SUMMARY

In accordance with one embodiment, a system and method of providing a confidence test for an assay includes determining a first quality metric based upon a first test environment and a second test environment wherein the second test environment is different from the first test environment, exposing a sample to a plurality of test sites, establishing the first test environment at a first of the plurality of test sites, establishing the second test environment at a second of the plurality of test sites, obtaining a first detection signal associated with the first of the plurality of test sites exposed to the sample and at the first test environment, obtaining a second detection signal associated with the second of the plurality of test sites exposed to the sample and at the second test environment, determining a second quality metric based upon the first detection signal and the second detection signal, and comparing the second quality metric with the first quality metric.

In accordance with another embodiment, a method of determining a quality metric includes exposing a control sample to a plurality of test sites, establishing a first test environment at a first of the plurality of test sites, establishing a second test environment at a second of the plurality of test sites, obtaining a first detection signal associated with the first of the plurality of test sites exposed to the control sample and at the first test environment, obtaining a second detection signal associated with the second of the plurality of test sites exposed to the control sample and at the second test environment, and determining a quality metric based upon the first detection signal and the second detection signal.

DESCRIPTION

Figure 1:
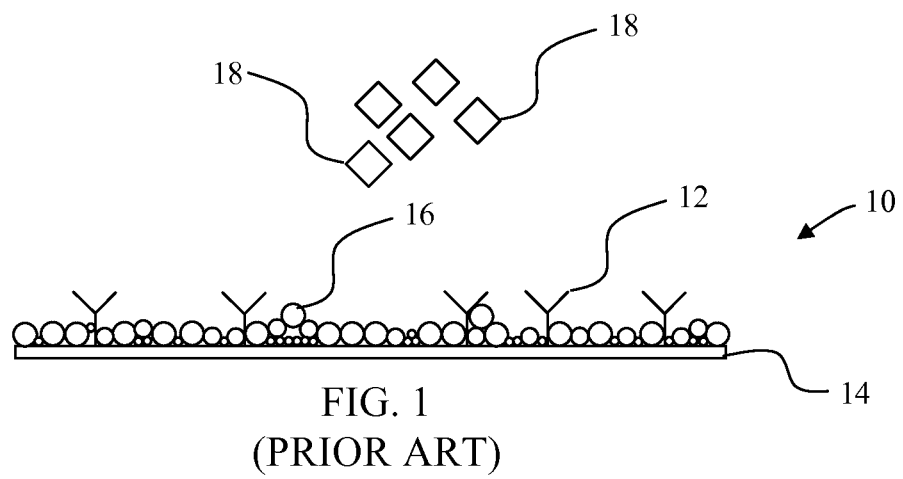
FIG. 1 depicts a schematic of a prior art test site within an ELISA array with an antibody and blockers formed on a substrate as a sample is added to the test site.
Figure 2:
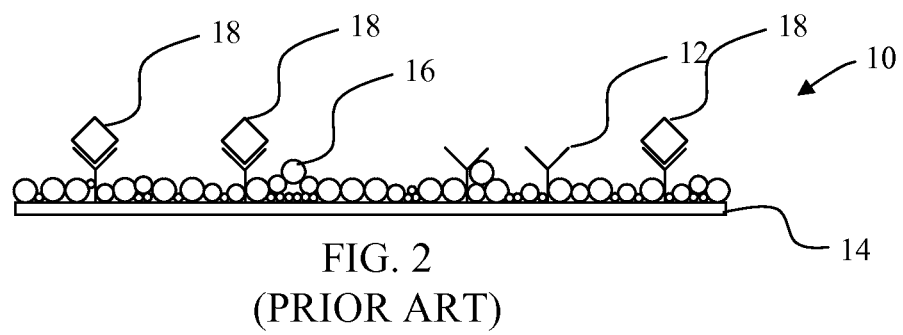
FIG. 2 depicts the test site of FIG. 1 with a molecule of interest bound to some of the antibodies of FIG. 1 after the test site has been incubated and washed.
Figure 3:
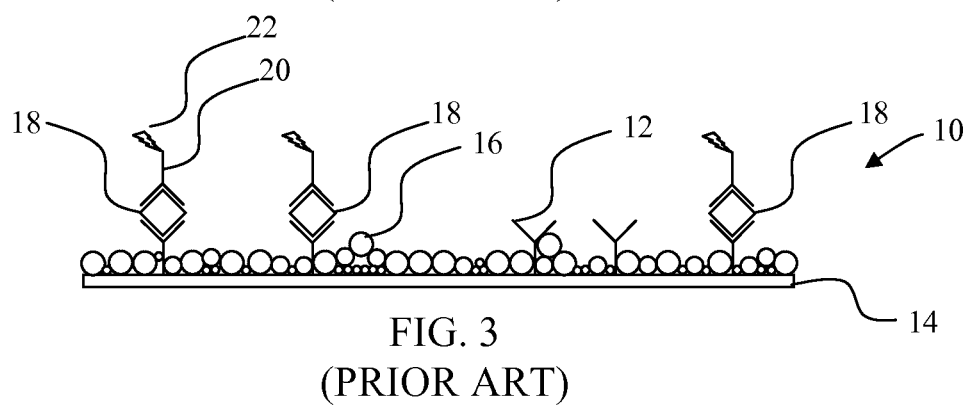
FIG. 3 depicts the test site of FIG. 2 after a labeled secondary antibody has been added and the test site has again been incubated and washed so that the labeled secondary is bound to the bound molecules of interest.
Figure 4:
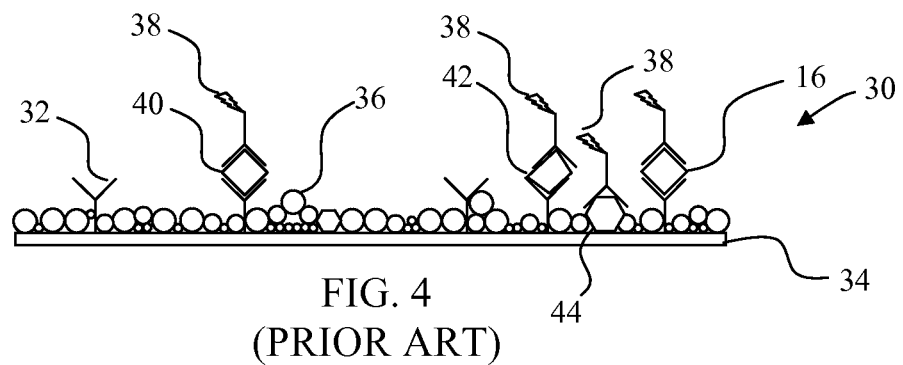
FIG. 4 depicts a schematic of a prior art test site within an ELISA array wherein a labeled secondary is bound to interfering molecules due to cross-reactivity and also physiosorbed to the surface of the substrate raising the background noise level of the test.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
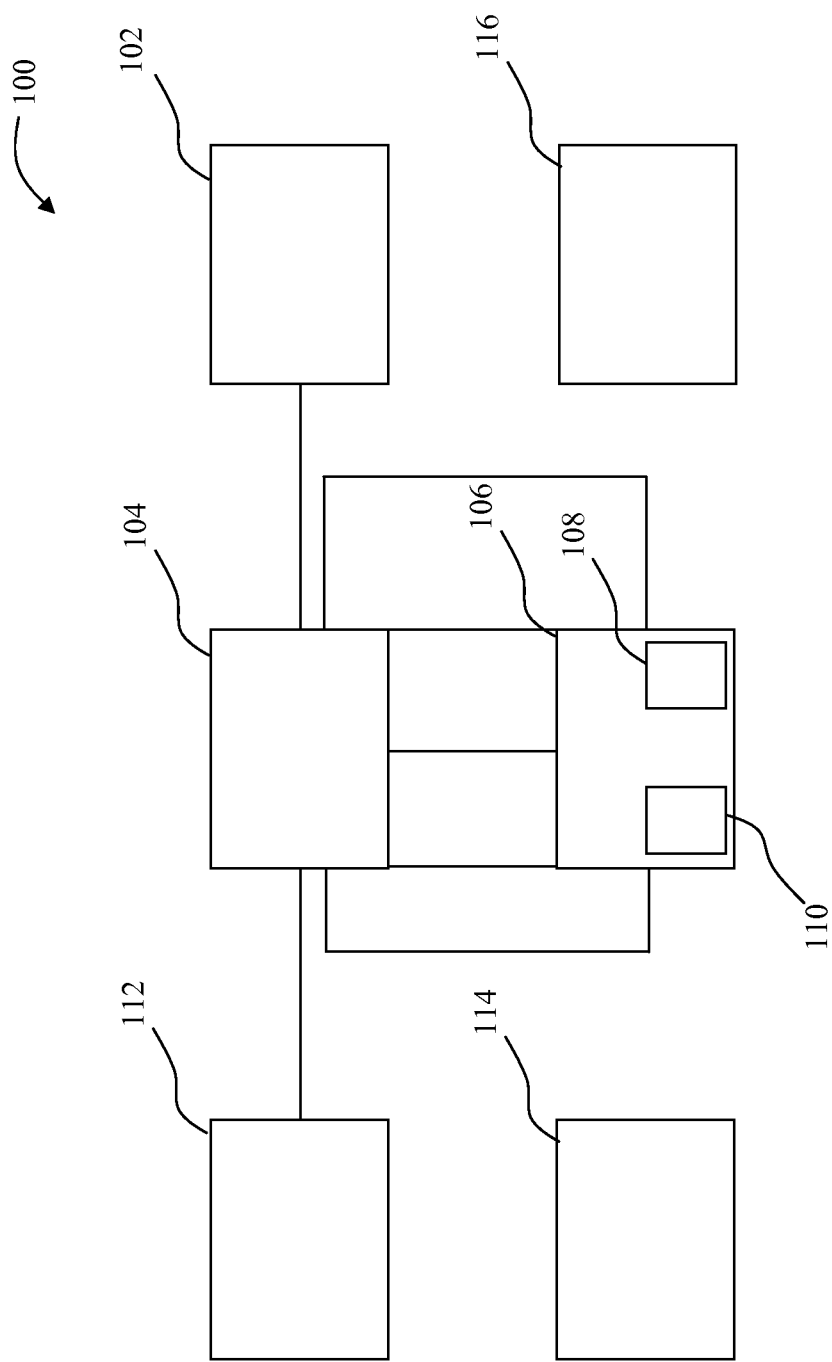
FIG. 5 depicts a multi-site biosensor system configured to control chemical environmental conditions at various test sites to modulate the affinity at the test sites for a molecule of interest.

Referring to FIG. 5, there is depicted a representation of a multisite biosensor system generally designated 100. The biosensor system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the biosensor system 100, and that allow internal information of the biosensor system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components of the biosensor system 100 as appropriate. Quality metrics databases 110 are also located within the memory 106.

The biosensor system 100 further includes environment control equipment 112 and environment detector suite 114. The environment control equipment 112 is configured to control the test conditions locally at different sites of a platform. One such control approach is described in U.S. patent application Ser. No. 12/580,113, filed on Oct. 15, 2009, the entire contents of which are herein incorporated by reference. Control of the test conditions locally at different sites of the platform can also be used to increase the dynamic range of the assay as described in U.S. patent application Ser. No. 12/688,193, filed on Jan. 15, 2010, the entire contents of which are herein incorporated by reference. An alternative to direct control of the test environment is indirect modification of an environmental condition as described in U.S. patent application Ser. No. 12/779,687, filed on May 13, 2010, the entire contents of which are herein incorporated by reference.

Figure 6:
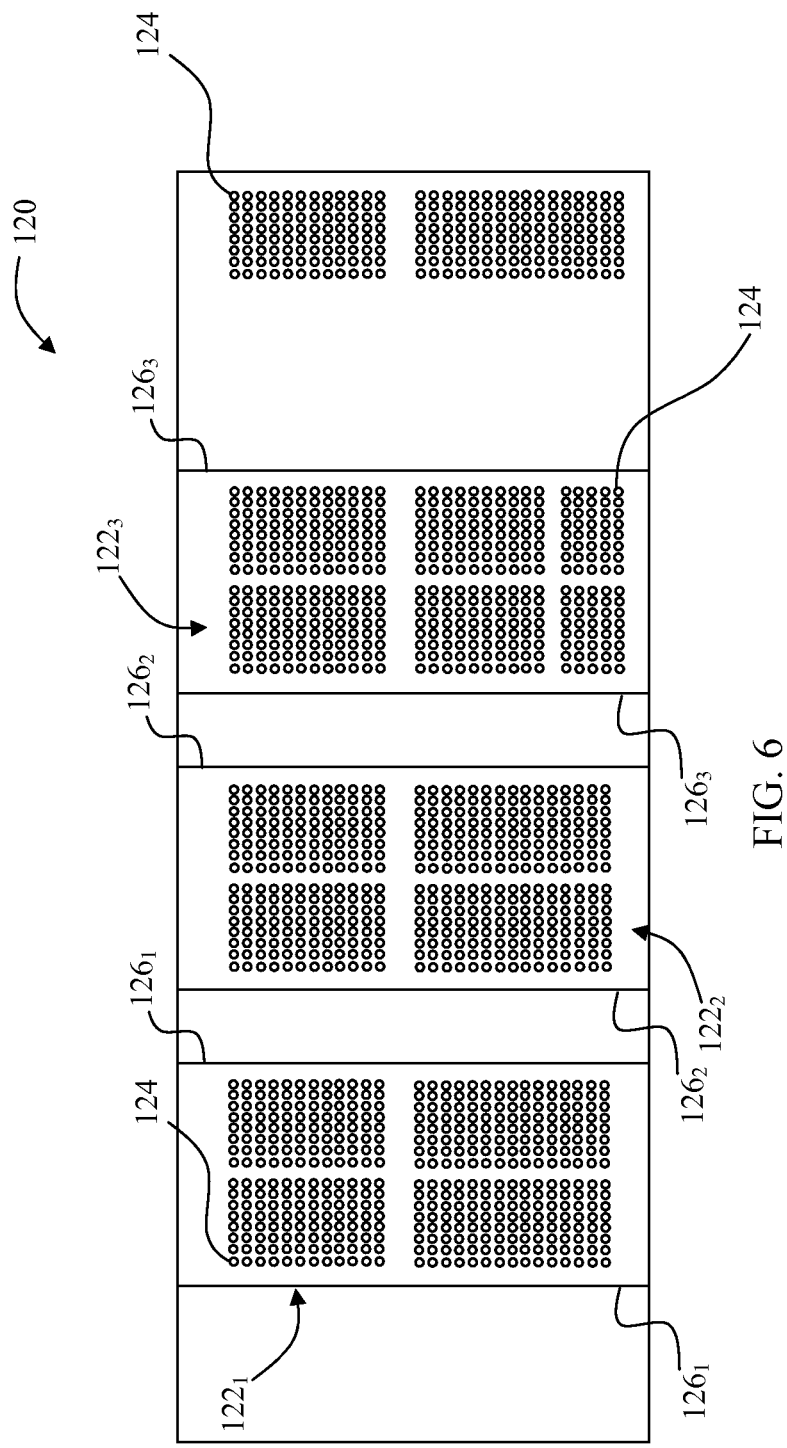
FIG. 6 depicts a platform for providing a number of different test sites in the form of a microarray.

The environment control equipment 112 in this embodiment is configured to control the test conditions locally at different sites of a microarray 120 depicted in FIG. 6. Various methods may be used to form the microarray platform 120. By way of example, U.S. Pat. No. 5,807,522 discloses a method for forming microarrays. The microarray platform 120 includes a number of different subarrays $122_X$. The subarrays $122_X$ include a number of test sites 124 which are prepared with a capturing agent effective for capturing a biomolecule of interest. Each of the subarrays $122_X$ is associated with a respective electrode pair $126_X$. The number and layout of subarrays $122_X$ and associated electrode pairs $126_X$, as well as the number of test sites 124 within each of the subarrays $122_X$ may be varied within the scope of the invention.

In one embodiment, the environment control equipment 112 is operable to establish a voltage profile within the microarray platform 120 using the electrode pairs $126_X$. The environment control equipment 112 is thus used to control the pH at each of the test sites 124 as described more fully in U.S. patent application Ser. No. 12/779,687. The precise pH within each of the test sites 124 may be detected by the detector suite 114. Sensors may be provided on the microarray platform 120 to assist in determining the precise pH within each of the test sites 124.

Returning to FIG. 5, the system 100 further includes a label reader 116. The label reader 116 may be included in a single device along with the other components of the system 100. Alternatively, one or more of the components of the system 100 may be provided as a separate device which may be remotely located from the other components of the system 100.

Figure 7:
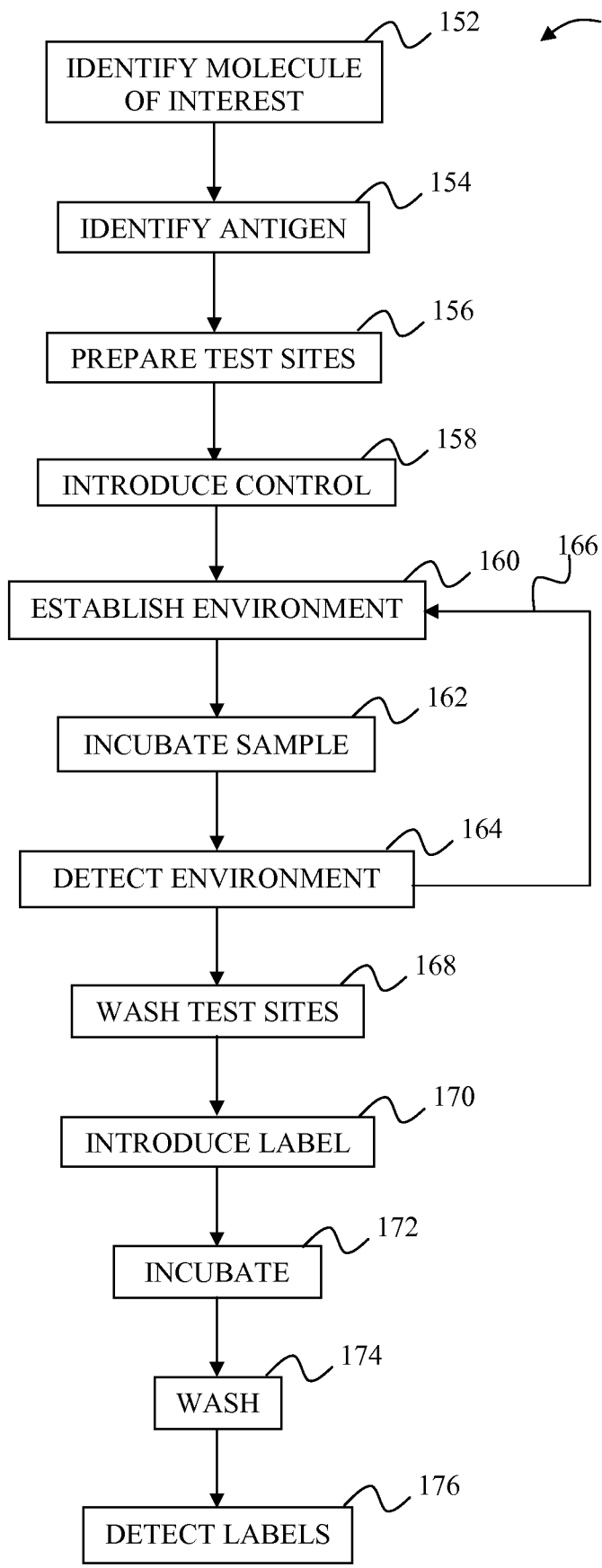
FIG. 7 depicts a procedure that can be used to expose a control sample to multiple test environments to obtain data for use in determining a quality metric for a molecule of interest in the control sample.

The biosensor system 100 may be used to determine a quality metric for one or more molecules of interest in a sample as detailed more fully with reference to the procedure 150 of FIG. 7. The processing circuit 104 executes the program instructions 108 to execute at least some of the procedure 150 of FIG. 7. In different embodiments, the procedure 150 may be modified to include more or fewer steps depending upon the specific criterion.

At block 152 of FIG. 7, a molecule of interest is identified and then an antibody with an affinity for the molecule of interest is identified (block 154). At block 156, the microarray platform 120 is prepared by depositing a desired amount of the selected antibody (probe molecules) with an affinity for the molecule of interest in each of the test sites 124. In alternative embodiments, a subset of the test sites 124 may be prepared with a first probe molecule while another subset of the test sites 124 may be prepared with a second probe molecule so as to allow two separate molecules of interest to be targeted within a single microarray platform 120. Additional configurations within a single microarray platform 120 may also be used. By way of example, each of the test sites within one of the subarrays 122 may be prepared with the same probe molecule while another of the subarrays 122 includes a different probe molecule.

Once the microarray platform 120 is prepared, a control sample is introduced into the selected set of test sites 124 (block 158). The "control sample" is a sample that either has a known composition or that exhibits, or comes from a source that exhibits, a known quality or characteristic. By way of example, a solvent with a known concentration of a molecule of interest may be used as a control sample. Additionally, a solvent with a known concentration of molecules of interest along with other molecules of known concentration may be used as a control sample. Even if the concentrations or identities of all of the molecules within a sample are not known, the sample may be used as a control sample if the sample is obtained from a source having a specific characteristic, e.g., a specific form of cancer, a known cancer-free source, etc.

If not already established, the environment within each of the selected set of test sites 124 is controlled to establish a different pH within each of at least two different test sites 124 (block 160). In alternative embodiments, other environmental factors may be controlled to provide a desired test site environment such temperature, electric field, magnetic field, and buffer type. The environmental factor or factors that are controlled are selected to provide two different thermodynamic conditions for the molecule of interest as described more fully below.

Once the test sites 124 are at the desired test environments (block 160), the sample is incubated at the established test environments for a predetermined time (block 162). During the incubation, the actual test environment within each of the selected set of test sites 124 is monitored by the environment detector suite 114 and data indicative of the established test environment is provided to the processing circuit 104 (block 164). The detected pH may be used by the processing circuit 104 to further control the environment control system 112 to precisely maintain the test environments established at the test sites 124 (block 166). When the sample has been sufficiently incubated, the test sites 124 are washed (block 168) and a labeled secondary antibody is introduced into the selected set of test sites 124 (block 170) and incubated (block 172). The selected set of test sites 124 are then washed (block 174) and the labels remaining in the test sites 124 are detected by the label reader 116 (block 176).

As discussed above, the test environment at each of two different test sites 124 is controlled to provide two different thermodynamic conditions. At each of the thermodynamic conditions, a different proportion of the molecule of interest will bind to the probe molecules. For example, a molecule of interest that has two different thermodynamic conditions at different pH environments may exist in a single chemical state at a lower pH and a higher pH. The affinity of the molecule of interest at each of the two pH levels, however, will vary. Thus, the proportion of the molecules of interest that are bound by the probe molecules for a sample having a particular concentration of the molecule of interest will vary depending upon the pH. This same relationship exists even for molecules of interest that exhibit complex behavior between two different thermodynamic conditions.

Figure 8:
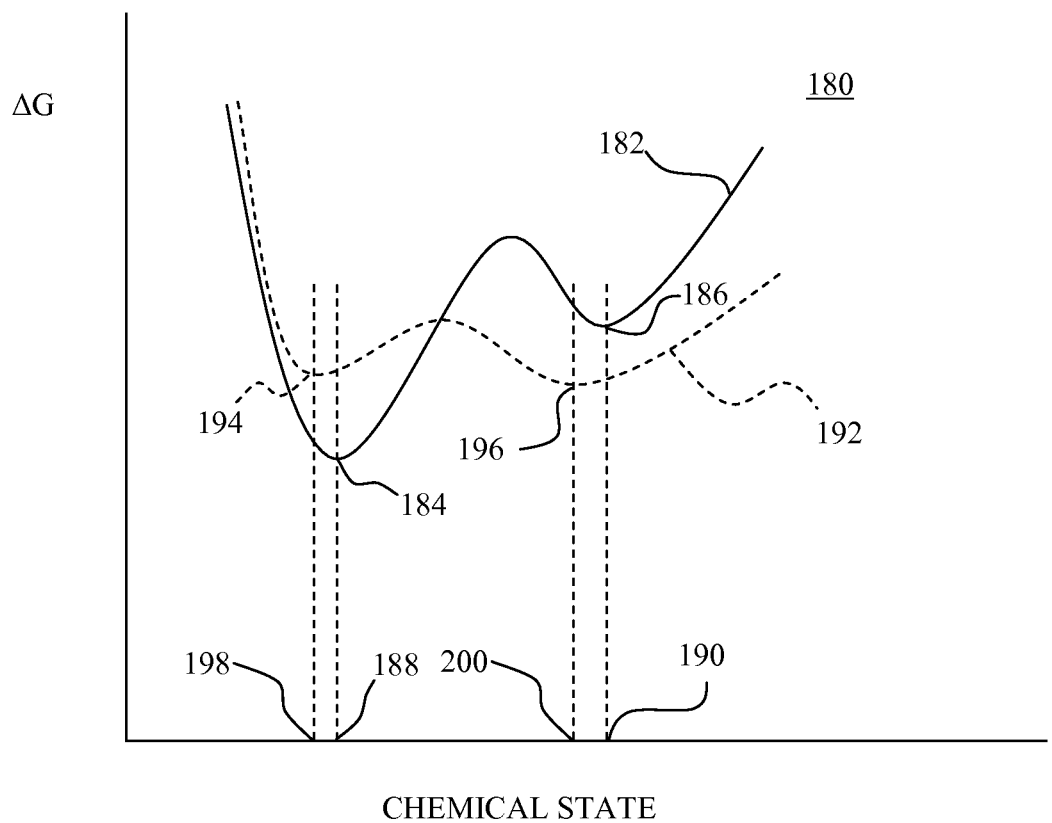
FIG. 8 depicts the Gibbs Free Energy ($\Delta G$) of different states of An exemplary molecule for two different environmental conditions which shows that at different environmental conditions two local minima of the molecule are different and the proportions of the molecule at the lower local minima with respect to the higher local minima in each of the two different environments is different.

More specifically, FIG. 8 shows a graph 180 including a line 182 that depicts an exemplary relationship between the Gibbs Free Energy ($\Delta G$) of a molecule and the chemical states of the molecule at a first set of environmental conditions which, for purpose of this example, may be a pH of 7. The line 182 includes two local minima 184 and 186. Accordingly, when a sample including the molecule is established in the first set of environmental conditions, the molecule will tend to form the two chemical states 188 and 190 associated with the local minima 184 and 186. The affinity of a given probe, however, will vary depending upon the particular chemical state. Accordingly, the number of molecules that bind with the probe is a function of the concentration of the molecule of interest at each of two different chemical states as well as two different binding affinities for each of the chemical states.

FIG. 8 further shows a line 192 that depicts an exemplary relationship between the ΔG of the molecule and the chemical states of the molecule at a second set of environmental conditions which, for purpose of this example, may be at a pH of 9. The line 192 includes two local minima 194 and 196. Accordingly, when a sample including the particular molecule is established in the second set of environmental conditions, the molecule will tend to form the two chemical states 198 and 200 associated with the local minima 194 and 196. The local minima 194 and 196, while similarly located to the local minima 184 and 186, are nonetheless at different chemical states. Even if the local minima were at the same chemical states, the shape of the line 192 is different from the shape of the line 182. This indicates that the proportions of molecules in the chemical state 194 will be less than the proportion of molecules in the chemical state 184 for a given concentration of the particular molecule within the control sample. Consequently, by establishing a first of the test sites 124 at a pH of 7 and a second of the test sites 124 at a pH of 9, two different thermodynamic conditions are established for the molecule of interest.

Thus, two different signals will be acquired by the label reader 116 from the two differently controlled test sites at the block 174. Accordingly, the signals obtained from the label reader 116 may be used to generate a quality metric ($Q_M$) for the molecule of interest in the control sample indicative of the variation in the proportion of the molecules of interest that are bound at each of the two thermodynamic states. In accordance with one embodiment, a quality metric is in the form of an end point difference quality metric. An end point difference quality metric is determined using the following equation:

$$Q_M = S_1(t_f) - S_2(t_f)$$

wherein $S_1$ is the signal obtained from a test site at a first test environment, $t_f$ is the final assay time after completion of the procedure 150, and $S_2$ is the signal obtained from a test site at a second test environment.

Depending upon the particular molecule of interest and other constituents in a control sample, an end point difference quality metric may not provide a convenient comparison metric. Accordingly, other forms of a $Q_M$ may be determined. By way of example, an end point normalized difference quality metric may be determined based upon the following equation:

$$Q_M = \frac{S_1(t_f) - S_2(t_f)}{S_1(t_f) + S_2(t_f)}$$

wherein $S_1$ is the signal obtained from a test site at a first test environment, $t_f$ is the final assay time after completion of the procedure 150, and $S_2$ is the signal obtained from a test site at a second test environment.

In other applications, a normalized rate of change $Q_M$ may be determined according to the following equation:

$$Q_M = \frac{S_1(t_f) - S_1(t_o)}{S_1(t_o)} - \frac{S_2(t_f) - S_2(t_o)}{S_2(t_o)}$$

wherein $S_1$ is the signal obtained from a test site at a first test environment, $t_f$ is the final assay time after completion of the procedure 150, $t_o$ is the assay time after a partial amount of the time of block 174, and $S_2$ is the signal obtained from a test site at a second test environment.

In yet another application, a normalized log rate of change $Q_M$ may be determined according to the following equation:

$$Q_M = \text{Log}\left[\frac{S_1(t_f) - S_1(t_o)}{S_1(t_o)}\right] - \text{Log}\left[\frac{S_2(t_f) - S_2(t_o)}{S_2(t_o)}\right]$$

wherein $S_1$ is the signal obtained from a test site at a first test environment, $t_f$ is the final assay time after completion of the procedure 150, $t_o$ is the assay time after a partial amount of the time of block 174, and $S_2$ is the signal obtained from a test site at a second test environment.

Once one or more $Q_M$ has been established from a control sample, the determined $Q_M$ for the control sample may be stored in the quality metrics databases 110.

While the proportion of a molecule of interest which binds with a probe molecule can be varied by controlling the test environment, the variation between the proportions of the molecule of interest that are bound at each of the two different thermodynamic conditions is consistent regardless of the initial concentration of the molecule of interest. Thus, the biosensor system 100 may be used to provide a quality metric for a sample with an unknown concentration of the molecule of interest as detailed more fully with reference to the procedure 210 of FIG. 9. The processing circuit 104 executes the program instructions 108 to execute at least some of the procedure 210 of FIG. 9. In different embodiments, the procedure 210 may be modified to include more or fewer steps depending upon the specific criterion.

Figure 9:
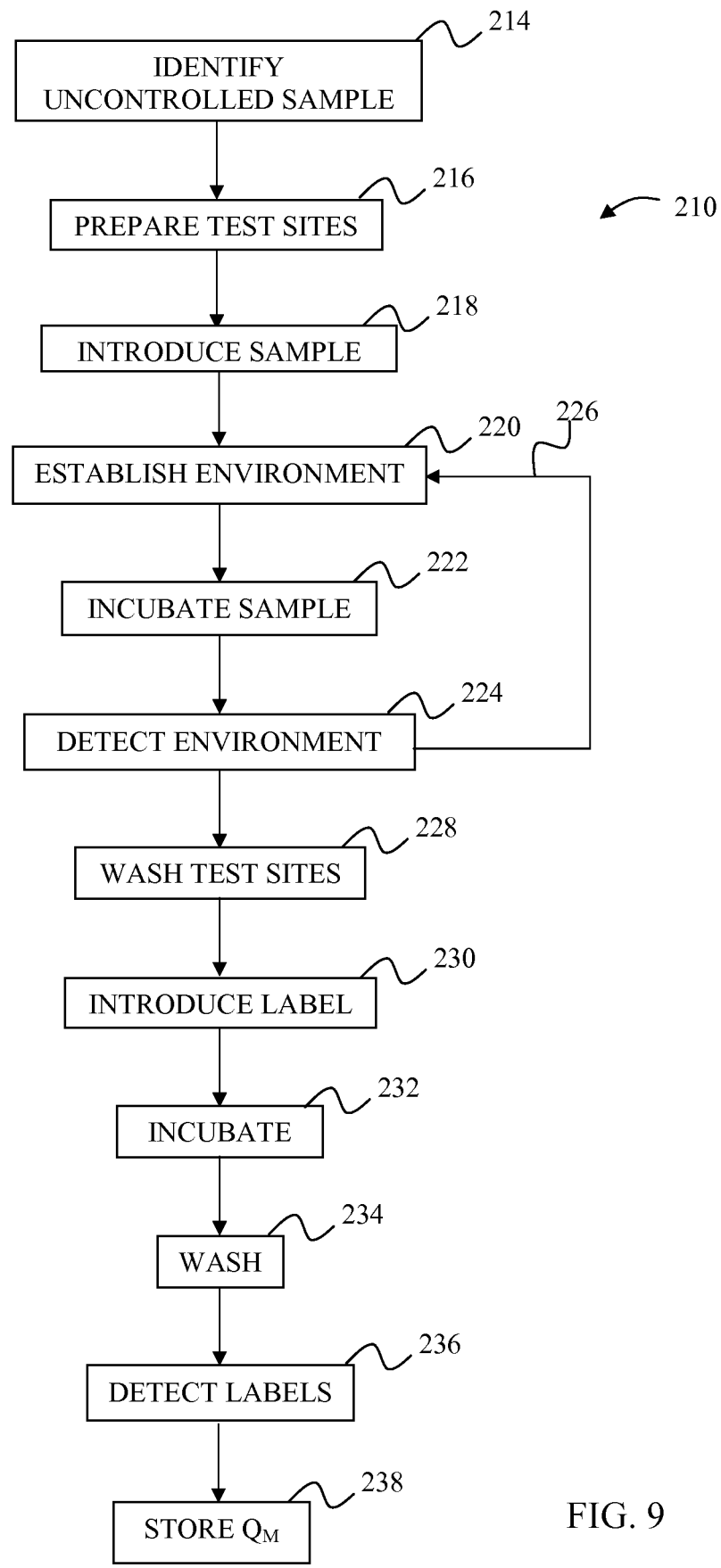
FIG. 9 depicts a procedure that can be used to expose an uncontrolled sample to multiple test environments to obtain data for use in determining a quality metric for a molecule of interest in the uncontrolled sample.

At block 214 of FIG. 9, an uncontrolled sample that is to be tested for the molecule of interest identified in block 152 of procedure 150 is identified. At block 216, the microarray platform 120 is prepared by depositing a desired amount of the antibody with an affinity for the molecule of interest (identified at block 154) in each of the test sites 124. If desired, the microarray 120 may be configured to test for multiple molecules of interest.

Once the microarray platform 120 is prepared, the uncontrolled sample is introduced into the selected set of test sites 124 (block 218). If not already established, the environment within each of the selected set of test sites 124 is controlled to establish a different pH within each of at least two different test sites 124 (block 220). In alternative embodiments, other environmental factors may be controlled to provide a desired test site environment such temperature, electric field, magnetic field, and buffer type. The environmental factor or factors that are controlled are selected to provide two different thermodynamic conditions for the molecule of interest. The two environments established should be the same two environments that were used in processing the control sample.

Once the test sites 124 are at the desired test environments (block 220), the uncontrolled sample is then incubated at the established test environments for a predetermined time (block 222). During the incubation, the actual test environment within each of the selected set of test sites 124 is monitored by the environment detector suite 114 and data indicative of the established test environment is provided to the processing circuit 104 (block 224). If desired, the data from the environment detector suite 114 may be used by the processing circuit 104 to maintain the established test environment at each of the two test sites (block 226). When the uncontrolled sample has been sufficiently incubated, the test sites 124 are washed (block 228) and a labeled secondary antibody is introduced into the selected set of test sites 124 (block 230) and incubated (block 232). The selected set of test sites 124 are then washed (block 234) and the labels remaining in the test sites 124 are detected by the label reader 116 (block 236).

At block 236, the signals obtained from the label reader 116 are used to determine a $Q_M$ for the molecule of interest in the uncontrolled sample. The $Q_M$ for the molecule of interest in the uncontrolled sample is determined using the same selected equation that was used to generate the $Q_M$ for the molecule of interest in the controlled sample and the determined the $Q_M$ is stored in the quality metric database 110 (block 238).

As discussed above, the quality metric for a given molecule of interest is consistent across samples regardless of the initial concentration of the molecule of interest in a particular sample so long as various parameters are consistent between the control sample and the uncontrolled sample. For example, so long as there are no new interfering molecules in the uncontrolled sample and so long as the uncontrolled sample is processed in the same manner as the control sample, the quality metric of the control sample and the uncontrolled sample will be comparable. Therefore, the $Q_M$ obtained from the uncontrolled sample may be used to perform a confidence test on the uncontrolled sample as detailed more fully with reference to the procedure 250 of FIG. 10.

Figure 10:
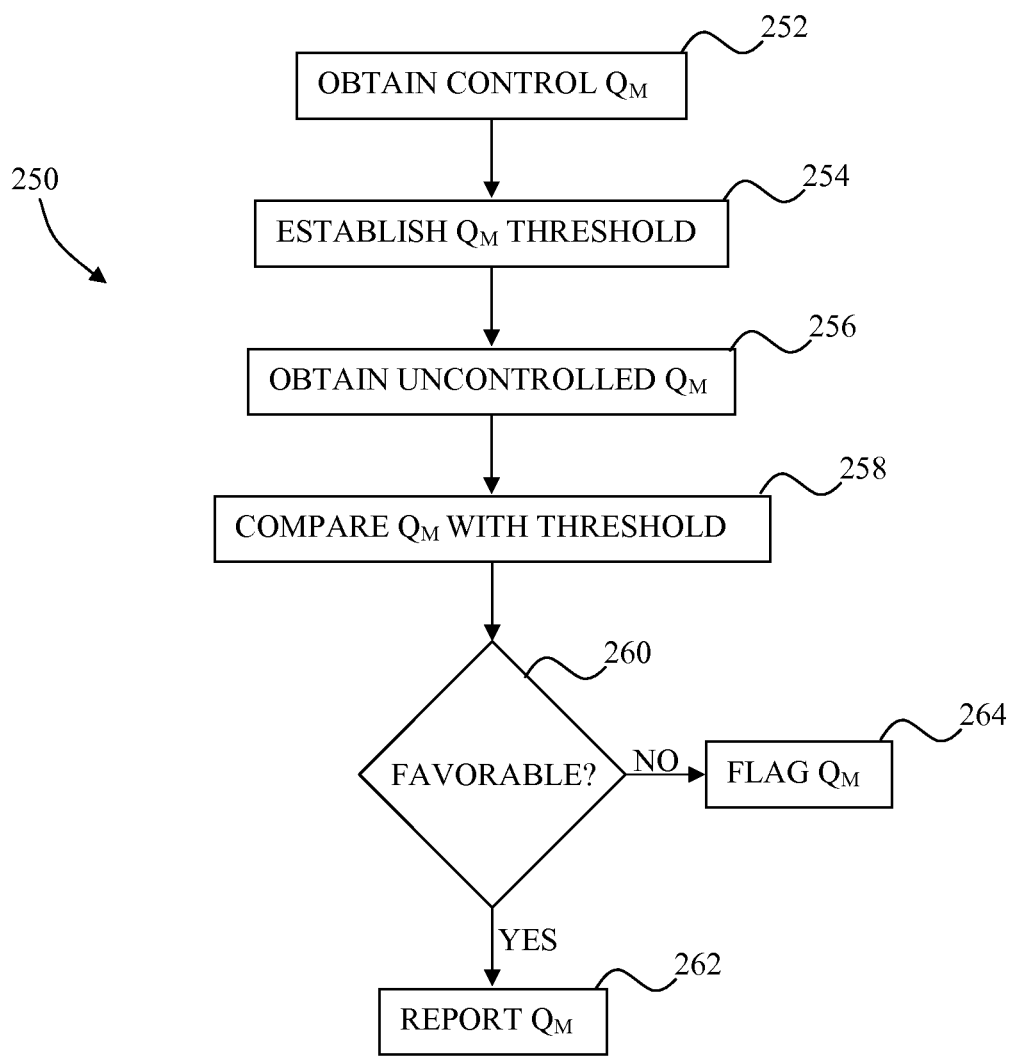
FIG. 10 depicts a procedure that can be used to compare the quality metric of a control sample with the quality metric of the uncontrolled sample to provide a confidence test on the uncontrolled sample.

With reference to FIG. 10, the processing circuit 104 executes the program instructions 108 to execute at least some of the procedure 250. In different embodiments, the procedure 250 may be modified to include more or fewer steps depending upon the specific criterion. At block 252, a value associated with the determined $Q_M$ of the control sample is retrieved from the quality metrics database 110. The retrieved value is used to establish a threshold confidence value at block 254. While in some embodiments the $Q_M$ of the control sample may be used directly to establish a confidence threshold, an acceptable range of values may be used. An upper confidence threshold may, for example, be 1.2 times the $Q_M$ of the control sample while a lower confidence threshold may be established at 0.8 times the $Q_M$ of the control sample.

At block 256 the $Q_M$ of the uncontrolled sample is obtained such as by retrieval from the memory 106 or by performance of the procedure 210. The $Q_M$ of the uncontrolled sample is then compared to the confidence threshold at block 258. If the $Q_M$ of the uncontrolled sample is within the confidence threshold range (a favorable comparison), then at block 260 the $Q_M$ of the uncontrolled sample and the results of the favorable comparison are reported. The results of the comparison may be in the form of the $Q_M$ of the uncontrolled sample divided by the $Q_M$ of the controlled sample. A favorable comparison indicates that the sample has been processed correctly and that any unknown molecules in the uncontrolled sample do not overly interfere with the binding of the molecule of interest to the probe molecules.

If the $Q_M$ of the uncontrolled sample is not within the confidence threshold range (an unfavorable comparison), then at block 262 the uncontrolled sample is flagged as outside of the desired accuracy of the test. If desired, the $Q_M$ of the uncontrolled sample and the results of the unfavorable comparison may be reported. An unfavorable comparison indicates that results obtained from the uncontrolled sample may not accurately indicate the amount of the molecule of interest in the sampled source. Inaccuracies may occur either because of improper handling of the sample or by unknown molecules in the uncontrolled sample that interfere with the binding of the molecule of interest to the probe molecules.

The procedures 150, 210, and 250 may thus be used to provide a confidence test for an array wherein a control sample is not required to be used on each multiplexed measurement platform. Quality metrics may further be used to provide insight into relationships between molecules. By way of example, to generate a network interaction map for a group of proteins, a sample of each of the proteins can be prepared and exposed to probe molecules associated with each of the other proteins. A normalized $Q_M$ for each of the associations can be determined using the procedure 150 wherein the two environments are identical for each of the samples.

Figure 11:
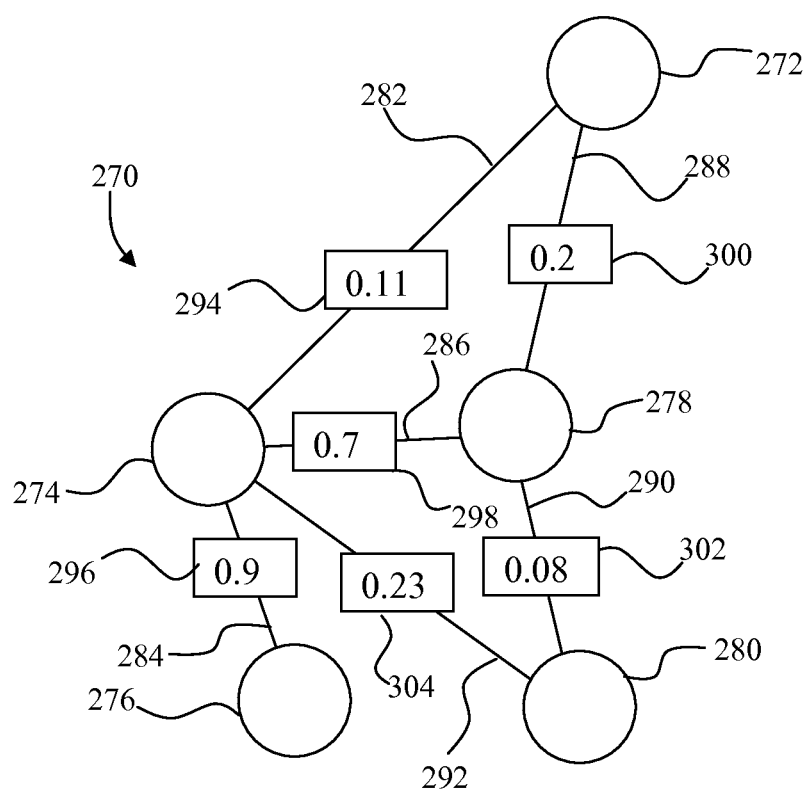
FIG. 11 depicts a network interaction map of proteins incorporating a weighted metric derived from quality metrics of the proteins which provides information as to the manner in which the proteins interact with each other.

Once normalized $Q_M$ values are obtained, a weighted network interaction map can be generated. By way of example, a protein interaction network 270 is depicted in FIG. 11. The protein interaction network 270 includes proteins 272, 274, 276, 278, and 280. Each of the proteins 272, 274, 276, 278, and 280 interact with one or more of the other of the proteins 272, 274, 276, 278, and 280 as indicated by the interaction lines 282, 284, 286, 288, 290, and 292. Thus, the protein interaction network 270 indicates that the protein 274 interacts with the protein 272 (interaction line 282), protein 278 (interaction line 286), protein 280 (interaction line 292), and protein 276 (interaction line 284).

FIG. 11 further includes, however, weighted values 294, 296, 298, 300, 302, and 304. The weighted values 294, 296, 298, 300, 302, and 304, which are normalized $Q_M$ values, provide insight as to the extent of the interaction between the various proteins 272, 274, 276, 278, and 280. Thus, while the protein 274 interacts with each of the proteins 272, 276, 278, and 280, the strongest reaction is with the protein 276 and the weakest reaction is with the protein 272. The normalized $Q_M$ thus represents a weighted value indicating the strength of the interaction between the proteins in the sample and the proteins associated with the probe molecules.

The generation of a quality metric for a sample has been experimentally verified using a system incorporating Indium Tin Oxide (ITO) electrodes fabricated on a glass slide by an etching process. The glass slide with the etched electrodes was then provided with a surface functionalization treatment by MicroSurfaces, Inc., of Austin Tex., to form a polyethyleneglycol (PEG) film anchored to the glass slide by silane coupling chemistry. In the experiment, antibody fragments (Immuno ChromPure Mouse IgG Fragment Fc, available from Jackson ImmunoResearch, West Grove, Pa.) were spotted on functionalized surfaces (NHS2, Microsurfaces Inc, Austin Tex.) which were subsequently incubated at three different voltages (0.0V, 0.25V and 0.5V) with an anti-mouse antibody (goat anti-mouse IgG H+L DyLight 549-conjugated, available from Jackson ImmunoResearch, West Grove, Pa.) to assess affinity to the IgG. The samples were then washed and read using an Axon Fluorescent scanner (commercially available from MDS Analytical Technologies, Sunnyvale, Calif.).

Three samples were used in the experiment. A first sample was used to provide a baseline reading. A second sample included PBS/PBS Tween 20, available from Sigma Aldrich, St. Louis Mo., in the incubation/washing buffer. A third sample included PBS/PBS Tween 20 mixed with 500 mM β-alanine, commercially available from Sigma Aldrich, St. Louis Mo., in the incubation/washing buffer.

Figure 12:
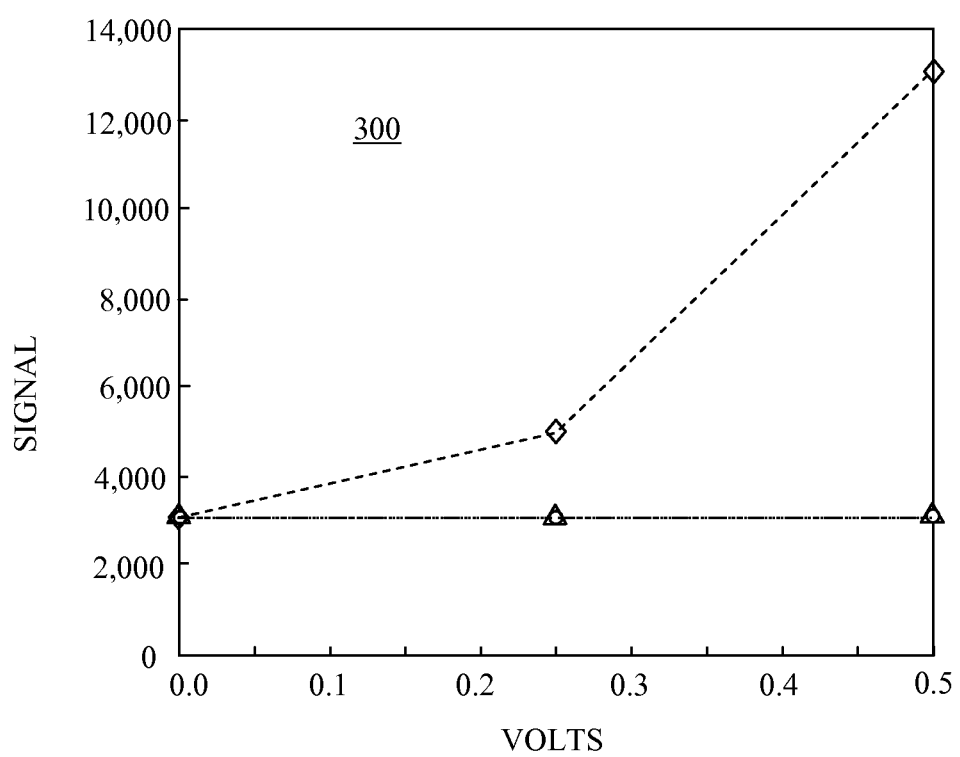
FIG. 12 depicts a graph of a detected signal for three samples of the same concentration of a molecule of interest at different voltages showing the effect on the affinity between the capture molecule at a test site and the molecule of interest when the two different environments are established at different test sites.

The results of the above described experiment are depicted in the graph 300 of FIG. 12 which depicts the normalized values obtained with the experiment. In FIG. 12, the readings of the first sample at 0.0V, 0.25V and 0.5V are indicated by a circle, the readings from the second sample are indicated by a triangle, and the readings using the third sample are indicated by a diamond. Each of the voltages provided an associated pH at the test sites. The graph 300 indicates that there were no significant differences in the readings between the baseline sample at the different voltages with a signal of about 3,000 counts, and a background noise level that was determined to be about 30 counts using the equations set forth above. Additionally, no noticeable change from the baseline measurements was obtained using the second sample at any of the three voltages.

Significant changes, however, were obtained with the third sample. At 0.0V, the graph 300 shows that a reading of 3000 counts was obtained. The graph 300 thus indicates that the addition of the β-alanine alone did not significantly alter the reading of the sample since the baseline sample also produced a reading of 3000 counts as discussed above. When a voltage of 0.25V was applied, the readings obtained from the third sample increased to a count of 5,000. A further increase was obtained by increasing the voltage to 0.5V. At 0.5V, a reading of about 13,000 counts was obtained. Additionally, the background contribution to the 13,000 counts was determined to be about 150 counts. An end-point normalized difference $Q_M$ of 0.08-6 was calculated based upon the obtained signals. Thus, modification of the test environment as discussed above with respect to the procedures 150 and 210 can be used to generate a quality metric for a molecule of interest.

A multisite biosensor for generating a quality metric for use in identifying a confidence test can thus be implemented on a printed circuit board, glass substrate, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The chip can be part of a system using stand alone microfluidics or a capillary principle or may be used with a separately provided device. The signal estimation and the assay data can be hard coded on the CMOS chip if desired. These platforms in some embodiments may be provided with an onboard environment control capability. Thus a lateral flow device may include printed electrodes which are powered by an on-board battery and controlled by an on-board processing circuit configured to execute one or more of the procedures 150, 210, and 250.

The type of sensor or sensors incorporated into the label reader 116 will vary depending upon the particular label used. Various embodiments may thus use luminescence, fluorescence, colorimetric, electrochemical, impedance, and magnetic sensors. The sensors can be configured to allow isolation of the signal produced by a selected one or more test sites. Likewise, the sensors incorporated into the environment detector suite 114 may include IR sensors, and Hall sensors. AMR sensors or GMR sensors may be provided to monitor the density of magnetic beads on a test site surface. ISFETs or CMOS based charge detection circuits may be used in electrochemical embodiments.

The procedures 150, 210, and 250 can thus be used in a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays, or other appropriate platforms. The procedures 150, 210, and 250 may further be used for generating a quality metric for a variety of molecules of interest as well as different types of molecules in addition to antibodies. By way of example, the procedures 150, 210, and 250 may also be used for generating a quality metric for a nucleic acid, protein, or small molecules. The procedures are not limited to binding processes, and can thus be extended to enzymatic reaction studies including phosphorylation studies, protein-protein interactions, protein nucleic acids interactions, and competitive assays.

In one embodiment, the procedures 150, 210, and 250 may be used to validate various tests. By way of example, U.S. Patent Publication No. 2003/0003516, published in Jan. 2, 2003, discloses a method for determining the anti-body specificity profile of an individual while U.S. Patent Publication No. 2008/0026485, published on Jan. 31, 2008 discloses compositions and methods for prognostic classification of autoimmune disease patients. The methods and devices disclosed by these and other publications allow rapid testing and identification of a large number of antibodies on a small platform. The increased spot density and sensitivity of such devices, however, can lead to increased false positives. Such false positives can be identified using procedures such as the procedures 150, 210, and 250.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:
1. A method of providing a confidence test for an affinity based assay without the need for a separate control sample, comprising:
determining, using a control sample having a known amount of molecules of interest, a first quality metric for the molecule of interest indicative of a variation in a proportion of the molecules of interest in the control sample that are bound on at least one first affinity based assay device at each of a first and a second thermodynamic state wherein the proportion of the molecules of interest in the control sample that are bound on at least one first affinity based assay device varies between the first and the second thermodynamic state, and wherein the first and second thermodynamic state are associated with a respective first test environment and second test environment wherein the second test environment is different from the first test environment;
establishing a threshold confidence value based upon the determined first quality metric;
exposing an uncontrolled sample having an unknown amount of the molecules of interest to a plurality of test sites on a second affinity based assay device, each of the plurality of test sites configured to bind the molecule of interest;

establishing, by executing with a processing circuit program instructions stored in a memory, the first test environment at a first of the plurality of test sites on the second affinity based assay device;

binding a first number of the molecules of interest of the uncontrolled sample at the first of the plurality of test sites;

establishing, by executing with the processing circuit the program instructions stored in the memory, the second test environment at a second of the plurality of test sites on the second affinity based assay device;

binding a second number of the molecules of interest of the uncontrolled sample at the second of the plurality of test sites, the second number different from the first number;

obtaining a first detection signal associated with the first number of bound molecules of interest;

obtaining a second detection signal associated with the second number of bound molecules of interest;

determining, by executing with the processing circuit the program instructions stored in the memory, a second quality metric for the molecule of interest indicative of a variation in a proportion of the molecules of interest in the uncontrolled sample that are bound on the second affinity based assay device at each of two thermodynamic states based upon the first detection signal and the second detection signal;

comparing, by executing with the processing circuit the program instructions stored in the memory, the second quality metric with the established threshold confidence value;

quantifying the amount of the molecules of interest using at least one of the first detection signal and the second detection signal; and determining, by executing with the processing circuit the program instructions stored in the memory, a confidence in the quantified amount of the molecules of interest based upon the comparison of the second quality metric with the established threshold confidence value.

2. The method of claim 1, wherein determining a first quality metric comprises:
exposing the control sample to a plurality of control test sites;
establishing the first test environment at a first of the plurality of control test sites;
establishing the second test environment at a second of the plurality of control test sites;
obtaining a third detection signal associated with the first of the plurality of control test sites exposed to the control sample and at the first test environment; and
obtaining a fourth detection signal associated with the second of the plurality of control test sites exposed to the control sample and at the second test environment.

3. The method of claim 2, wherein determining a first quality metric comprises:
obtaining the third detection signal at a first final assay time;
obtaining the fourth detection signal at a second final assay time; and
identifying the first quality metric based upon a difference between the third detection signal and the fourth detection signal.

4. The method of claim 3, wherein determining a first quality metric comprises determining the first quality metric based upon a normalized difference between the third detection signal and the fourth detection signal.

5. The method of claim 3, wherein determining a first quality metric comprises:
obtaining a fifth detection signal associated with the first of the plurality of control test sites exposed to the control sample and at the first test environment at a first initial assay time;
obtaining a sixth detection signal associated with the second of the plurality of control test sites exposed to the control sample and at the second test environment at a second initial assay time; and
identifying the first quality metric based upon a normalized rate of change between the fifth signal and the third signal and between the sixth signal and the fourth signal.

6. The method of claim 5, wherein determining the first quality metric comprises:
determining the first quality metric based upon a logarithmic of the normalized rate of change between the fifth signal and the third signal and between the sixth signal and the fourth signal.

7. The method of claim 2, wherein exposing a control sample to a plurality of control test sites comprises:
exposing a control sample with known constituents in known proportions to the plurality of control test sites.

8. The method of claim 2, wherein exposing a control sample to a plurality of control test sites comprises:
exposing a control sample with a known characteristic to the plurality of control test sites.

9. The method of claim 1, wherein:
establishing the threshold confidence value includes establishing a range of values based upon the first quality metric; and
determining the confidence in the quantified amount of the molecules of interest includes determining that the second quality metric is within the range of values.

10. The method of claim 1, wherein:
establishing the first test environment comprises controlling at least one environmental factor of a group of environmental factors consisting of temperature, electric field, magnetic field, pH, and buffer type for the first test site; and
establishing the second test environment comprises controlling the at least one environmental factor of the group of environmental factors consisting of temperature, electric field, magnetic field, pH, and buffer type for the second test site such that the controlled at least one environmental factor is different between the first test site and the second test site.

11. The method of claim 10, wherein:
the second affinity based assay device is a glass slide;
establishing the first test environment comprises controlling the at least one environmental factor at a first portion of the glass slide; and
establishing the second test environment comprises controlling the at least one environmental factor at a second portion of the glass slide.

12. The method of claim 10, wherein:
the second affinity based assay device is a lateral flow device;
establishing the first test environment comprises controlling the at least one environmental factor at a first portion of the lateral flow device; and establishing the second test environment comprises controlling the at least one environmental factor at a second portion of the lateral flow device.

13. The method of claim 10, wherein:
the second affinity based assay device is a CMOS chip;
establishing the first test environment comprises controlling the at least one environmental factor at a first portion of the CMOS chip; and
establishing the second test environment comprises controlling the at least one environmental factor at a second portion of the CMOS chip.

14. The method of claim 1, wherein comparing the second quality metric with the first quality metric comprises:
establishing a range of values based upon the first quality metric; and
determining that the second quality metric is outside of the range of values, and wherein determining a confidence comprises:
identifying the quantified amount as inaccurate based upon the comparison of the second quality metric with the first quality metric.

15. The method of claim 1, wherein the second affinity based assay device is an affinity based assay device selected from the group consisting of a well plate, a microarray platform, a printed circuit board platform, a CMOS chip platform, a multiplexed assay, a protein array, a lateral flow device, a sandwich assay, a competitive assay, and a bead based array.

16. The method of claim 15, wherein the second affinity based assay device is an enzyme-linked immunosorbent assay (ELISA) well plate.

17. The method of claim 1, wherein determining the second quality metric ($Q_M$) for the molecule of interest comprises:
determining an end point difference quality metric based upon the following equation:

$$Q_M = S_1(t_f) - S_2(t_f)$$

wherein
$S_1$ is the first detection signal,
$t_f$ is a final assay time, and
$S_2$ is the second detection signal.

18. The method of claim 1, wherein determining the second quality metric ($Q_M$) for the molecule of interest comprises:
determining an end point normalized difference quality metric based upon the following equation:

$$Q_M = \frac{S_1(t_f) - S_2(t_f)}{S_1(t_f) + S_2(t_f)}$$

wherein
$S_1$ is the first detection signal,
$t_f$ is a final assay time, and
$S_2$ is the second detection signal.

19. The method of claim 1, wherein determining the second quality metric ($Q_M$) for the molecule of interest comprises:
determining a normalized rate of change quality metric based upon the following equation:

$$Q_M = \frac{S_1(t_f) - S_1(t_o)}{S_1(t_o)} - \frac{S_2(t_f) - S_2(t_o)}{S_2(t_o)}$$

wherein
$S_1$ is the first detection signal,
$t_f$ is a final assay time,
$t_o$ is an assay time after a partial amount of the final assay time, and
$S_2$ is the second detection signal.

* * * * *